United States Patent [19]

Guiset

[11] 4,044,401
[45] Aug. 30, 1977

[54] ARTIFICIAL BLADDER

[76] Inventor: Jacques Guiset, 62, rue E., Delesalle Lille (Nord), France

[21] Appl. No.: 711,209

[22] Filed: Aug. 3, 1976

[30] Foreign Application Priority Data

Aug. 4, 1975 France .............................. 75.25283

[51] Int. Cl.² .............................................. A61F 1/24
[52] U.S. Cl. ................................................. 3/1; 3/1.2;
128/DIG. 25
[58] Field of Search ......... 3/1, 1.2; 128/1 R, DIG. 25

[56] References Cited

U.S. PATENT DOCUMENTS

| 3,750,194 | 8/1973 | Summers | 3/1 |
| 3,953,897 | 5/1976 | Chevallet et al. | 3/1 |

FOREIGN PATENT DOCUMENTS

| 2,116,838 | 7/1972 | France | 3/1 |

*Primary Examiner*—Ronald L. Frinks

*Attorney, Agent, or Firm*—Robert E. Burns; Emmanuel J. Lobato; Bruce L. Adams

[57] ABSTRACT

The present invention relates to an artificial bladder. It is characterized in that it comprises a leak-proof enclosure wall, which internally forms a closed cavity accessible through two upper apertures and through one lower aperture, means for connecting each of the upper apertures to a ureter, means for connecting the lower aperture to the urethra, a small balloon made of leak-proof, flexible material, which is positioned inside the said cavity and forms a closed space internally, means for introducing a fluid at will into the said small balloon and for extracting it from there so as to inflate and deflate it respectively, means for sealing the two upper apertures, which are open when at rest, and means for opening the lower aperture, which is closed when at rest, when the said small balloon is inflated, so as to induce urination. Its use is either to replace the bladder in the case of ablation or to re-establish the normal functions of a defective bladder.

20 Claims, 1 Drawing Figure

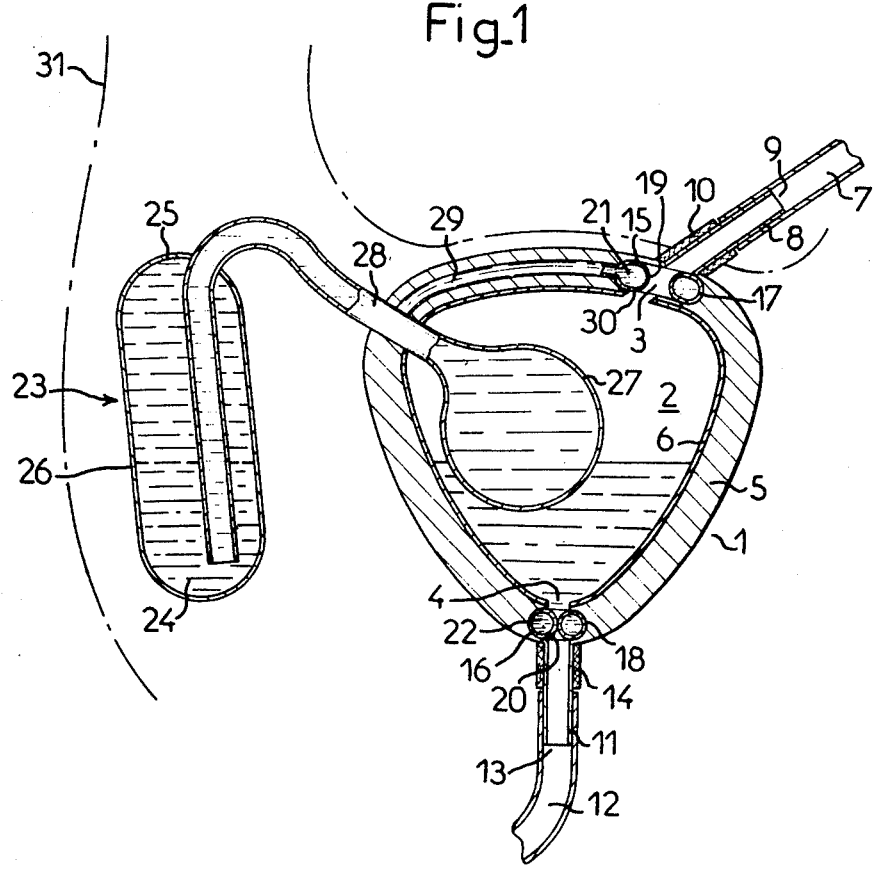

ARTIFICIAL BLADDER

BACKGROUND OF THE INVENTION

The present invention relates to an artificial bladder. By artificial bladder we include for example, a natural bladder with artificial parts.

It is known at the present time that ablation of the bladder, which seems to be unavoidable for example in the case of a tumour, is always followed by placing two ureters next to the skin, since there are no appliances amongst medical equipment capable of replacing the bladder's characteristics of capacity and ability to contract.

Placing ureters next to the skin in this way does not normally allow the treated subject to lead a normal life.

On the other hand, in the case of urination difficulties or incontinence, methods in use are known which partly compensate the bladder's functions, i.e., electrical stimulation of the anal sphincter to induce urination and, in the case of incontinence, placing a KAUFMAN appliance in the form of a cushion upon the posterior urethra.

But these two methods are only palliatives, as in no case do they re-establish normal functioning, given on the one hand the irksome nature of electrical stimulation and, on the other hand, the low efficiency of the appliance.

The object of the present invention is to offer the subject suffering from impairments to the bladder in all or part of its functions the possibility of nevertheless leading a normal life, and particularly of inducing independent urination.

SUMMARY OF THE INVENTION

This aim is fulfilled, in accordance with the invention, by means of an appliance capable of being substituted for the bladder in the case of ablation of the latter, and different parts which can be used separately in a natural malfunctional bladder in order to palliate the functional impairments relating to urination of the latter.

Comprising a leak-proof enclosure wall, which internally forms a closed cavity accessible through two normally open upper apertures, each one of which can be connected to one of the ureters, and through one normally closed lower aperture, which can be connected to the urethra, the artificial bladder in accordance with the invention is capable of replacing the natural bladder's role as a reservoir.

The artificial bladder in accordance with the invention also comprises a balloon, which can be inflated at will and is positioned inside this cavity, and means for sealing the two upper apertures and opening the lower aperture when the balloon is inflated; this allows independent urination to be induced. It should be observed that these units can also be used separately, and cooperate with a natural bladder, of which only certain functions are maintained, in order to compensate its defective functions; in particular, in the case of difficulty in urination, the small inflatable balloon can readily be placed inside the natural bladder by means of a minor operation, replacing the electrical stimulators, compared with which it has the advantage of total autonomy and actual agreeable functioning.

The artificial bladder in accordance with the invention is characterized in that it comprises a leak-proof enclosure wall internally forming a closed cavity which is accessible through two upper apertures and through one lower aperture, means for connecting each of the upper apertures to a ureter, means for connecting the lower aperture to the urethra, a balloon made of leak-proof, flexible material which is positioned inside the said cavity and internally forms a closed space, means for selectively introducing a fluid into the said balloon or for extracting it therefrom so as to inflate and deflate it respectively, means for sealing the two upper apertures, which are normally open and means for operating the lower aperture, which is normally closed, when the said balloon is inflated so as to induce urination.

Of course, when possible, the leak-proof enclosure wall can be formed by the subject's own bladder.

BRIEF DESCRIPTION OF THE DRAWINGS

The invention will be better understood through reference to the description below, referring to a non-restrictive method of arrangement, and also to the attached drawing which forms an integral part of this description.

This single drawing shows FIG. 1 as a view in section of the set of parts of an artificial bladder in accordance with the invention in its most complete form, replacing the natural bladder.

DESCRIPTION OF PREFERRED EMBODIMENT

A leak-proof enclosure wall 1 is shown which internally forms a closed cavity 2, accessible through two upper apertures such as 3 (only one of which appears here) and by a lower aperture 4.

This enclosing wall 1 is intended to be a substitute for the natural bladder's role of urine reservoir, and externally is preferably of a pseudo-pyramidal shape related to that of a natural bladder so that it can be implanted into the space normally occupied by the latter.

The enclosing wall 1 is preferably rigid and defined by an external wall 5, made for example of hard, molded plastic which gives it its shape, and by an absolutely leak-proof internal wall 6.

Each of the two upper apertures 3 of the enclosing wall 1 is designed to be connected to a ureter such as 7. To this end, the enclosing wall 1 comprises a tube 8, which is integral with the rigid wall 5 and designed to have the ureter, such as 7, slipped on externally, around each of the apertures 3 and protruding towards the exterior of enclosing wall 1; each of the tubes 8 is preferably wide-mouthed, near its extremity 9, which is the one furthest away from the enclosing wall, so as to improve its hold after slipping on at least for a while following the operation. Moreover, the anastomosis of the ureter such as 7 with the artificial bladder in accordance with the invention is preferably facilitated by a collar 10, which is made of an appropriate material such as a velvet of synthetic fibres already currently employed for such uses. The collar 10 lines tube 8 on the outside between the extremity of ureter 7 and the external surface of the rigid wall 5 of enclosing wall 1.

Similar arrangements are to be found at the level of the lower aperture 4 of the enclosing wall, which extends outwards by means of a tube 11 onto which the urethra 12 is slipped externally. This tube 11 is preferably wide-mouthed near its extermity 13, the one furthest from enclosing wall 1, and is coupled externally between urethra 12 and the external surface of rigid wall 5 of enclosng wall 1, made of a material 14 which is designed to facilitate the anastomosis of the appliance with urethra 12.

Around each of the apertures such as 3 and 4, the artificial bladder in accordance with the invention comprises parts which form sphincters which are normally open at the level of the upper apertures 3 and normally closed at the level of the lower aperture 4; moreover, these sphincters must be capable respectively of closing and opening at will when it is desired to induce urination.

These parts which form sphincters can be made in the shape of BJORK-type or STARR-type valves, such as those which are frequently used in heart surgery, but a preferred type of arrangement has been represented to the single drawing, in accordance with which each of the sphincters is constituted by an inflatable collar 15 and 16 respectively, positioned around each aperture 3 and 4 in a ring-shaped groove, 17 and 18 respectively, which is fitted in the rigid wall 5 of the enclosing wall 1 around this aperture and open towards it.

Each of collars 15 and 16 has at least one internal surface which is elastically deformable, 19 and 20 respectively, and means to induce at will deformation of this internal surface, so that it closes up upon itself so as to seal the aperture or so that it opens, in this way clearing it.

The elastically deformable internal surface of each collar 15 and 16 can advantageously be defined by a leak-proof wall which may be deformed elastically by the collar and facing which the collar internally forms a leak-proof, ring-shaped cavity, closed by this wall so as to be leak-proof.

In the illustrated example collars 15 and 16 are constituted by a hollow toric part made of leak-proof, elastically deformable material; each of these toric parts internally forms a ring-shaped chamber, 21 and 22 respectively.

Each of the collars such as 15, which line the upper apertures such as 3, is usually open to allow access to urine, but the device in accordance with the invention comprises means to close it at the time of urination.

These means comprise here a reservoir 23 of fluid 24 to which the inner chamber 21 of each colar such as 15 is connected by a passage such as 29 which can be partly immersed in rigid wall 5 of enclosing wall 1.

The reservoir 23 is placed outside the enclosing wall 1 so as to be readily accessible by hand. For example, it is positioned underneath the skin at pubis level, preferably forming an arched shape for this purpose so that it is adapted to the pelvic girdle.

It is defined by a leak-proof wall 25, which at least towards the front has a flexible zone 26, suited to receive an impulse from the outside which is transmitted to fluid 24 so as to expel the fluid from the reservoir towards chamber 21 of each sleeve 15, inducing the inner surface 19 of the collar to close upon itself and the sealing of the aperture such as 3.

Regarding the lower aperture 4, this is closed outside urination periods and it does not seem absolutely necessary to provide it with a device to induce it to open when it is desired to induce urination: chamber 22 of collar 16 is filled with a fluid at a fixed pressure, and this collar which is normally closed, is opened when pressure in cavity 2 increases above a predetermined threshold and following an impulse upon flexible zone 26 of reservoir 23 of fluid 24 by means of a device which shall now be described.

This device, designed to increase in a moment and at will the pressure inside cavity 2, particularly when the cavity is filled with urine, essentially comprises a small balloon 27 which is made of leak-proof, flexible and preferably elastic material and is positioned inside cavity 2 internally forming a closed space connected by passage 28 to reservoir 23. (it should be observed that passage 29 leading to chamber 21 of each collar such as 15 can possibly be diverted into this passage 28, as illustrated).

When pressure is applied to flexible zone 26 of reservoir 23, fluid 24 is expelled on the one hand towards the small balloon 27 which inflates, and on the other hand towards chamber 21 of sleeve 15 lining each of the upper apertures 3, which closes.

It is advantageous if each of the tubes 8 linked with a ureter 7 is inclined in relation to the perpendicular towards the wall of enclosing wall 1 in close proximity to the tubes 8, so that the increase in the pressure in cavity 2 following the increase in volume of small balloon 27 tends to facilitate closing of the collar 15 by applying pressure to them in zone 30 facing cavity 2.

Moreover, the reliability in use of the device can be augmented by shaping and arranging the small balloon 27 so that it abuts against the upper apertures 3 when inflated.

In order to allow complete emptying of the bladder through the action of the small balloon 27, the balloon's maximum volume is at least equal to that of the cavity 2, due, of course, to a coefficient of adequate safety, and the maximum volume of the reservoir 23 is at least equal to that of the small balloon 27. In practice these three volumes can be equal, for example in the region of 300 $cm^3$.

In order to free the cavity 2 so as to allow it to fill up again after being emptied, devices are provided to induce the return of the fluid contained in the small balloon 27 towards the reservoir 23 as soon as emptying is finished. In practice, for example, reservoir 23 is depressed in relation to the small balloon 27, either by positioning at a mean level lower than the level of the small balloon, or by mechanical means. The flexible zone 26 of wall 25 can advantageously take over this role, if it is elastic, by sucking fluid towards reservoir 23 when the manual pressure applied onto it is released.

However, the small balloon 27 should preferably never be completely emptied of the fluid which it contains so that the progressive filling-up of cavity 2 with urine has the effect of applying pressure to it, which is transmitted to the reservoir 23 and to its flexible zone 26, producing on the subject a sensation informing him on the full state of his bladder.

The use of such an emptying device having a small balloon 27 is in no way limited to the only complete artificial bladder, and it would not be stepping outside the framework of the invention to use it with a natural bladder, for example a paralytic one. The artificial sphincters described could, of course, also be adapted to compensate a functional impairment of the sphincters of a natural bladder.

In certain particular cases it can happen that the arch-shaped reservoir 23 is replaced by a cylindrical cavity having a depression similar to that used in surgery in REDON drainage. This eventuality can occur in particular morphological cases where the reservoir 23 could not be adapted to the pubis, or when the natural retained bladder is prolapsed inside the strait of the pelvic girdle.

In the case of a complete artificial bladder similar to the one which has been described above by way of example, the functioning of the device in accordance with the invention is as follows.

When at rest, the upper apertures 3 are open, the lower aperture 4 is closed, the small balloon 27 is largely deflated and the reservoir 23 is generally full. The cavity 2 is cleared and can progressively fill with urine via the upper apertures 3.

When the volume of urine contained in the cavity 2 approaches the latter's maximum volume, the small balloon 27 is subjected to a pressure which induces gradual evacuation of the fluid 24, which it contains, towards the reservoir 23, which warns the subject that his bladder is filling. If the pressure in the cavity 2 increases above the measuring pressure of the lower flexible collar 16, it is possible that some drops of urine may escape through the ureteral meatus.

The subject then uses his hand to press upon his abdominal wall 32 at the level of the pubis, thus giving an impulse to the fluid 24 so that it flows from the reservoir 23 via the flexible zone 26 of the wall 25. This has the effect, on the one hand, of closing the upper apertures 3 by inflating the collar such as 15 and, on the other hand, of inflating the small balloon 27, which produces a great increase in pressure in the cavity 2 and, when this pressure becomes greater than the measuring pressure of the lower collar 16, draining-off of urine via the latter.

When the cavity 2 is empty, the pressure of fluid 24 decreases in the small balloon 27 and in the collar such as 15; the lower aperture 4 closes, while the upper apertures 3 open again.

At the end of the operation the fluid 24 originally contained in the reservoir 23 has passed towards the small balloon 27, but the depression in the reservoir 23 induces the return of the fluid towards the reservoir until the small balloon 27 reaches its original volume.

The device is then ready for a new cycle.

In order to produce the different parts of the artificial bladder in accordance with the invention, the most suitable materials should be chosen, in particular those which would avoid inflammation and rejection. For example, the equipment should be completely siliconed on the outside and the joins should be effected using siliconed adhesive. In order to make collar 10 and 14 so that they ensure anastomosis of the artificial bladder with the ureters and the urethra, a material should be chosen such as a velvet of synthetic fibres such as those commercially known under the name "DACRON". Regarding tubes 8 and 11 which are partially covered by these collars, these are made in silicone elastomer, for example, such as "SILASTIC."

Regarding the small balloon 27, collars 15 and 16, which form sphincters, and the leak-proof wall 6, which lines cavity 2 internally, these should be made of inalterable material, in particular insensitive to urinary ammonia. Flexible elastic rubber could be used for example.

Regarding the passage 28 forming a link between the small balloon 27 and the reservoir 23, this should be made of siliconed plastics material, in the same way as the reservoir 23.

It should be observed that the device which has just been described is subject to numerous variations without stepping outside the framework of the invention.

It must be noted, however, that this type of arrangement is particularly recommended as the risk of failure is slight. Moreover, parts which are possibly liable to be defective can be easily changed.

Indeed, all parts of the device are readily interchangeable by means of simple operations, with the exception of the rigid wall 5 of enclosing wall 1 which serves only as a support on which the other parts are fixed and which, consequently, runs no risk of being damaged.

Deflation of the lower collar 16, which is the most frequent risk, can readily be compensated by reflation of this collar by means of a needle; the elastic texture of this collar makes this operation possible.

If this ruptures, likewise the upper collar 15, a new collar can be put into place, which can be introduced, when the collar is deflated, into the corresponding ring-shaped groove and then inflated. In the particular case of the upper collar 15, it is possible to make these in the shape of a hollow toric part identical to the lower collar 16, passage 29 terminating in a needle valve (not shown here) protruding into the ring-shaped groove 17 so as to penetrate chamber 21 of collar 15 when the latter is placed in the groove.

Should the small balloon 27 rupture, it is easy to replace it externally either by means of carrier forceps inserted inside the cavity 2, or from the reservoir 23 in which an incision is made for this purpose.

This incision is easy to make, likewise the possible changing of this reservoir 23, since it is placed immediately underneath the skin.

Regarding leakages due to cicatrization defects at the level of the join to the ureters and the urethra, these can be avoided by retaining permanent catheterization during the 2 or 3 months following the operation.

In this way, the invention offers simplicity of use and viability which, coupled with the fact that it allows total or possibly only partial compensation of the bladder function by establishing rythmical urination of the individual's secretion and by making the subject aware at all times of the state of fullness of his bladder, allow the treated individual to lead quite a normal life, and this advantage is increased still more by the device's autonomy and the fact that it is completely implanted.

I claim:

1. An artificial bladder characterized in that it comprises: a leak-proof enclosure wall internally forming a closed cavity which is accessible through two upper apertures and through one lower aperture, means for connecting each of the upper apertures to a ureter, means for connecting the lower aperture to the urethra, a balloon made of leak-proof, flexible material which is positioned inside the said cavity and internally forms a closed space, means for selectively introducing a fluid into the said balloon or for extracting it therefrom so as to inflate and deflate it respectively, means for sealing the two upper apertures, which are normally open and means for opening the lower aperture, which is normally closed when the said balloon is inflated so as to induce urination.

2. A bladder in accordance with claim 1, characterized in that the enclosure wall is pseudo-pyramidal in shape externally, similar to the shape of a natural bladder.

3. A bladder in accordance with claim 1 characterized in that the enclosure wall comprises a rigid external wall which is lined internally by a leak-proof wall.

4. A bladder in accordance with claim 1 characterized in that the balloon is made of elastic material.

5. A bladder in accordance with claim 4 characterized in that the means for introducing a fluid at will into the balloon or for extracting it therefrom comprises a fluid reservoir defined at least partially by a flexible wall, which is arranged to receive an impulse from outside which is transmitted to the fluid, and a passage linking the said reservoir to the said space inside the balloon so as to inflate the latter during the said impulse.

6. A bladder in accordance with claim 5 characterized in that the fluid reservoir, in use, is mounted at a lower level than the balloon.

7. A bladder in accordance with claim 5 characterized in that the reservoir is arch-shaped on the outside so that it adapts to the pelvic girdle.

8. A bladder in accordance with claim 7 characterized in that the reservoir has a flexible front wall and a rigid rear wall.

9. A bladder in accordance with claim 1 characterized in that the balloon is positioned so that, when inflated, it abutts against the two upper apertures so as to seal them.

10. A bladder in accordance with claim 1 characterized in that the means for sealing an upper aperture when the balloon is inflated comprise a collar which is integral with the said enclosure wall surrounding the said aperture, and has at least one elastically deformable inner wall normally defining a central passage and means to selectively produce a deformation of the said inner surface so that it closes upon itself to close said passage.

11. A bladder in accordance with claim 10 characterized in that the elastically deformable inner wall of said collar is leak-proof and said collar includes a ring-shaped cavity, which is closed and in that the means for producing deformation at will of the inner wall comprises a fluid reservoir, defined at least partially by a flexible wall designed to receive an impulse from outside which is transmitted to the fluid, and a passage linking the said reservoir to the said ring shaped cavity.

12. A bladder in accordance with claim 1 characterized in that the means for closing the lower aperture when at rest and for opening it when the balloon is inflated comprises a collar, which is integral with the said enclosure wall and which surrounds the said lower aperture, and has at least one elastically deformable inner wall, normally closed upon itself to close the lower aperture and adapted to open under the increase in pressure in the said cavity following inflation of the balloon.

13. A bladder in accordance with claim 12 characterized in that the means for closing the lower aperture when at rest and for opening it when the balloon is inflated comprise a hollow toric part made of leak-proof material, which is elastically deformable and permanently inflated.

14. A bladder in accordance with claim 10 characterized in that around each aperture provided with a collar the enclosure wall has a ring-shaped groove, which is open towards the aperture and is designed to receive the said collar inside it.

15. A bladder in accordance with claim 1 characterized in that around each aperture and protruding outwards in relation to the enclosure wall the connecting means comprise a tube, which is integral with the enclosure wall and is capable of having a ureter or the urethra slipped onto it.

16. A bladder in accordance with claim 15, characterized in that each tube is wide-mouthed close to its end remote from the enclosure wall.

17. A bladder in accordance with claim 15 characterized in that, between the enclosure wall and the ureter or the urethra respectively, each tube comprises externally a sleeve made of material suitable for producing anastomosis with the latter.

18. A bladder in accordance with claim 15 characterized in that the tubes of the upper apertures are inclined towards the enclosure wall adjacent the enclosure wall.

19. A bladder in accordance with claim 1 characterized in that the maximum volume of the balloon is at least equal to the volume of the cavity defined by the enclosure wall.

20. A bladder in accordance with claim 5 characterized in that the maximum volume of the reservoir is at least equal to the maximum volume of the balloon.

* * * * *